United States Patent [19]

Ketner et al.

[11] Patent Number: 5,776,745
[45] Date of Patent: Jul. 7, 1998

[54] RECOMBINATIONALLY TARGETED CLONING IN YEAST ARTIFICIAL CHROMOSOMES

[75] Inventors: Gary Wayne Ketner, Columbia; Philip Andrew Hieter, Baltimore; Janice E. Clements, Columbia, all of Md.

[73] Assignee: The Johns Hopkins University, Baltimore, Md.

[21] Appl. No.: 540,721

[22] Filed: Oct. 11, 1995

Related U.S. Application Data

[62] Division of Ser. No. 96,771, Jul. 23, 1993, abandoned.

[51] Int. Cl.⁶ .............................. C12N 15/10; C12N 1/19
[52] U.S. Cl. ...................... 435/172.3; 435/254.2; 435/254.21
[58] Field of Search ................. 435/172.1, 172.3, 435/320.1, 240.2, 252.3, 254.2, 254.21; 536/23.1, 23.74, 23.72

[56] References Cited

U.S. PATENT DOCUMENTS 4,889,806  12/1989  Olson et al. .................. 435/172.3

*Primary Examiner*—David Guzo
*Attorney, Agent, or Firm*—Fish & Richardson, P.C.

[57] ABSTRACT

Homologous recombination techniques are used to produce yeast artificial chromosomes (YAC) containing foreign target DNA by utilizing at least three DNA segments which yield the vector. Preferred embodiments allow the production of viral DNA which is infectious.

15 Claims, 9 Drawing Sheets

FIG. IA
FIG. IB
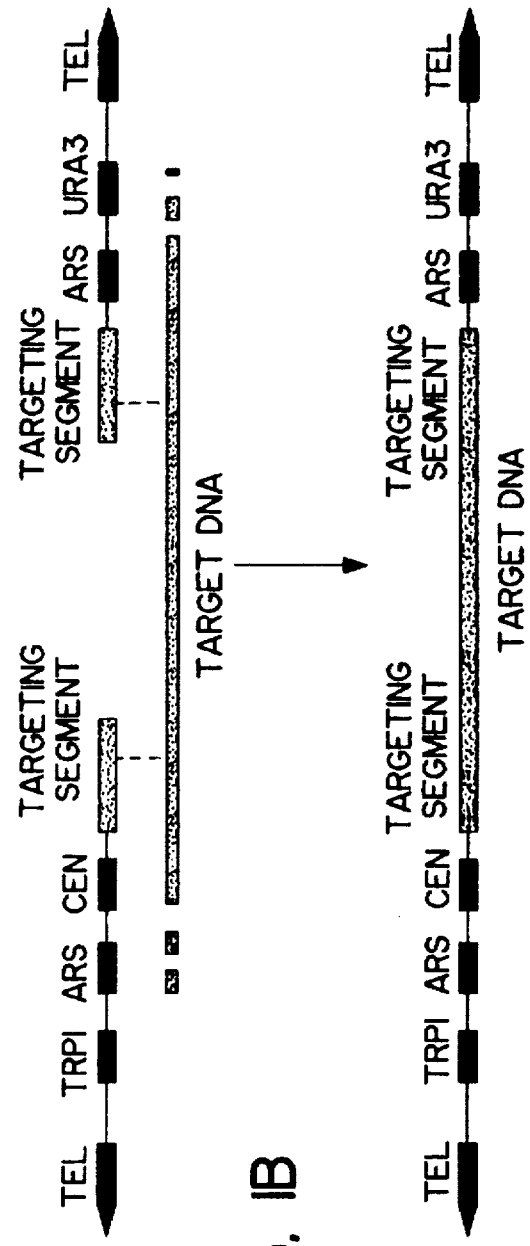
FIG. IC

RECOMBINATIONALLY TARGETED CLONING IN YEAST ARTIFICIAL CHROMOSOMES

This is a divisional of application Ser. No. 08/096,771 filed Jul. 23, 1993, now abandoned.

This invention was made with Government support under grant No.s AI 26239 and 5PO1 HG00373 05 from the National Institutes of Health. The Government has certain rights in this invention.

BACKGROUND OF THE INVENTION

1. Field of the Invention

This invention relates to recombinatorial cloning and specifically to the use of homologous recombination to produce yeast artificial chromosomes (YACs) containing foreign target DNA. The methodology of the invention is particularly useful for large target DNA such as infectious viral sequences.

2. Description of Related Art

Genetic recombination can be broadly divided into homologous recombination and site-specific recombination. These pathways are distinguished by their substrate DNAs, recombination patterns, and mechanisms. Homologous (general) recombination mediates exchanges between DNA segments that share extensive sequence homology, whereas site-specific recombination promotes rearrangements between DNA segments that lack extensive homology. In homologous recombination, exchange can occur at any point between homologous regions, although particular DNA sequences may influence the frequency of exchange.

DNA sequences cloned into yeast artificial chromosomes (YACs) have become useful tools in the genetic analysis of complex genomes. YACs are generally constructed by the in vitro ligation of bulk DNA preparations to appropriate vectors, followed by transformation into yeast cells. Typically, this methodology requires determining compatible splice junctions between the vector DNA and the foreign DNA which is to be expressed. However, where the expression product of the foreign DNA is a structural protein(s), the design and selection of appropriate ligation regions between the vector DNA and foreign DNA is laborious and, generally, serendipitous. Consequently, YACs produced by existing methodology usually contain random DNA segments, and YACs incorporating particular DNA segments must be identified among large numbers of irrelevant YACs by tedious screening procedures.

There are a variety of applications for which an efficient method for producing YAC clones of specific DNA segments would be valuable. Among these are the rapid cloning of mutant alleles of genes that are associated with genetic diseases, and the cloning of segments of DNA not represented in existing libraries of DNA sequences. In addition, it is desirable to clone viral DNA genomes for use as vectors, as well as other purposes.

The use of viruses as vectors for the transfer of foreign genes is important in such areas as the production of vaccines, genetic therapy and genetic engineering of commercially important animals and plants. Unfortunately, many viruses of clinical importance must rely upon cell culture techniques which are slow, laborious and produce small quantities of virus. Using available technology, such as that described above, the genetic modifications required to make a virus suitable as a vector are difficult to accomplish by conventional genetic engineering techniques. In the case of viruses, production is further complicated by the large size of the viral genome, the length of time required for growth of the virus in tissue culture, and the dependence of conventional genetic engineering techniques for fortuitously-located restriction enzyme cleavage sites.

The Adenoviruses are among the most widely-exploited experimental model systems for the study of basic eukaryotic molecular biology. Adenoviruses also promise to be valuable vectors for the delivery of exogenous genes to whole organisms or to individual cells for the purposes of vaccination and genetic therapy. The study of basic adenoviral biology and the development of adenoviral vectors both require manipulation of the viral genome;in the first case for the production of viral mutants, and in the second to incorporate exogenous DNA into the viral genome and to optimize its expression. Manipulation of adenoviral DNA is possible using current technology, but the schemes employed are time-consuming. As a consequence of the limitations imposed by existing methodology for producing and manipulating YACs, there is a need for a method of cloning large sequences of DNA, such as viral genomic sequences, which eliminates the need for in vitro ligation to produce YACs comprising large foreign DNA segments, such as viruses and allow genetic modification of the cloned foreign DNA segment as well. The present invention provides such a method.

SUMMARY OF THE INVENTION

The present invention is based on the discovery of a method for producing a yeast artificial chromosome (YAC) containing a foreign target DNA sequence by utilizing homologous recombination techniques. The method comprises combining at least three DNA segments by homologous recombination under permissible conditions wherein the DNA segments comprise a) a target DNA sequence; b) a first vector which contains a first targeting segment DNA sequence homologous to the 5' terminus region of the target DNA sequence; and c) a second vector which contains a second targeting segment DNA sequence homologous to the 3' terminus region of the target DNA sequence.

The invention also provides a composition comprising a YAC having a foreign target sequence and also a yeast cell which contains the composition comprising a YAC and a target sequence.

In another embodiment, the invention provides a method for the production of a target foreign DNA sequence, for example a viral genome sequence, which comprises culturing the composition including the YAC having the target foreign sequence under conditions which allow replication of the composition.

BRIEF DESCRIPTION OF THE DRAWINGS

FIG. 1 (Parts A–C). 1A shows pRML1 and pRML2; 1B shows the three DNA sequences which form the YAC-target sequence of the invention; 1C shows the assembled YAC-target sequence after homologous recombination.

FIGS. 1–4 Abbreviations: AMP: ampicillin resistance determinant, CYH2: recessive resistance allele of yeast CYH2 gene; DED: yeast DED1 promoter; GAL: yeast gal promoter; HSV TK: herpes simplex virus thymidine kinase gene. LEU2: yeast LEU2 gene. ori: colE1 origin of replication. TEL: yeast telomeric sequences. TRP1: yeast TRP1 gene. URA3: yeast URA3 gene.. Names in small type indicate sites for restrictions endonuclease cleavage. Dashed lines indicate the locations of recombination events.

DETAILED DESCRIPTION OF THE INVENTION

Figure 2A:
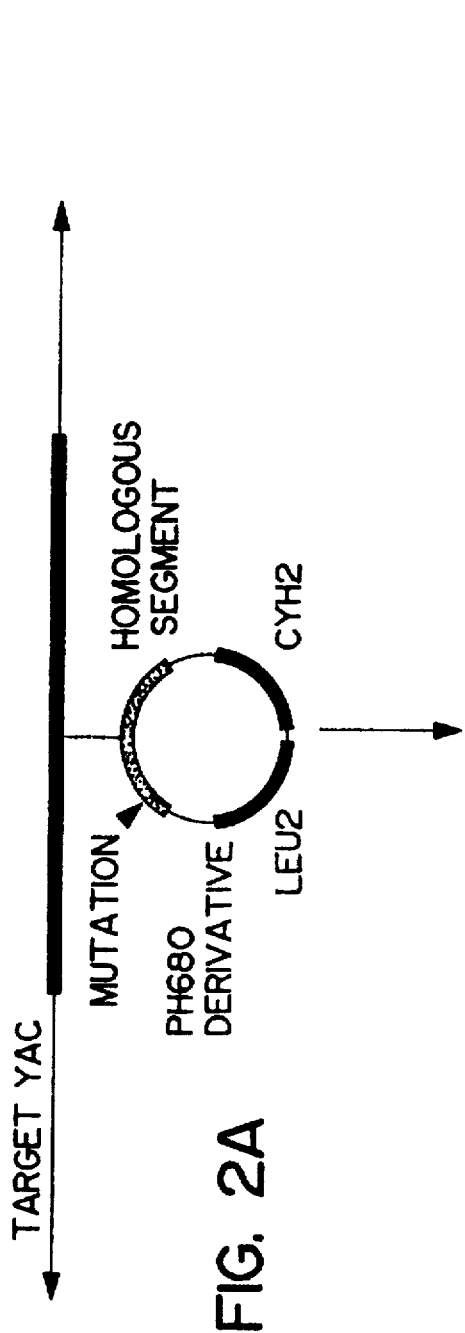
FIG. 2 (Parts A–C) is a schematic diagram of the two-step gene replacement technique.

The present invention provides a method for the production of a yeast artificial chromosome (YAC) which contains a foreign target DNA sequence. such as a viral DNA sequence. The method of the invention now allows the cloning and manipulation of large DNA sequences, such as viral genomes. which previously were difficult to clone by existing in vitro ligation techniques. The production of large amounts of viral DNA will be valuable as vectors useful for the delivery of exogenous genes to whole organisms or to individual cells for the purposes of vaccination and genetic therapy.

The term. YACs. refers to plasmids which are capable of replication in a yeast host and which are able to accommodate large pieces of DNA, up to several hundred kilobase pairs in length. As used herein, the term "foreign target DNA sequence" or "foreign target sequence" refers to a non-yeast DNA sequence which is selected to be cloned into a YAC vector by homologous recombination. Preferably the foreign target DNA sequence of the invention is a viral DNA sequence. The term "targeting segment DNA sequence" refers to a DNA sequence which is homologous to the flanking region of the target DNA sequence. The targeting segment DNA sequences of the invention are homologous to the 5' terminal region of the target DNA sequence or to the 3' terminal region of the target DNA sequence.

The invention provides a method for producing a YAC containing a target DNA sequence which comprises combining at least three DNA segments by homologous recombination under conditions which allow homologous recombination (i.e., permissive conditions). wherein the DNA segments minimally comprise: a) a target DNA sequence; b) a first vector which contains a first targeting segment DNA sequence homologous to the 5' terminal region of the target DNA sequence; and c) a second vector which contains a second targeting segment DNA sequence homologous to the 3' terminal region of the target DNA sequence (FIG. 1).

Preferably. the target sequence is a virus DNA sequence. The virus may be an RNA virus or a DNA virus. When the virus is an RNA virus. such as a retrovirus. proviral DNA is the preferred source of nucleic acid. The virus may be a DNA virus. such as adenovirus. herpes virus. human immunodeficiency virus (HIV). simian immunodeficiency virus (SIV). and vaccinia virus for example. Any viral genome could be used as the target sequence according to the invention. as long as the flanking termini are known, or can be ascertained. so that the termini can be used as targeting segments. Other large segments of DNA. such as human chromosomal DNA or genomes of other higher organisms may also be used as target DNA sequences in the method of the invention.

The targeting segments of the invention are DNA sequences homologous to the flanking regions of the foreign target sequence. Typically. the targeting segments are at least about 15 nucleotides in length and sufficiently homologous to the flanking region of the target sequence to allow the targeting segment to mediate exchange by homologous recombination with the target sequence.

The targeting segments are cloned into prototype YAC vectors which include different types of sequences which allow propagation and. preferably. selection of hosts containing the vector. The sequences in the vectors supply the cisacting genetic elements required for YAC maintenance in yeast (telomeres. a centromere. and origins of replication). and genetic markers used to select yeast cells containing the final YAC product. These sequences may include: 1) a CEN sequence. which provides all the cis-acting information required to confer mitotic and meiotic centromere function on DNA molecules introduced into yeast; 2) an ARS sequence (autonomous replication sequence) in order to replicate as autonomous molecules; 3) a TEL sequence. which is required for telomere formation; 4) an interruptible marker containing a cloning site. for example SUP4-o gene. an ochre-suppressing allele of a tRNA$^{Tyr}$ gene; and 5) yeast selectable markers. such as TRP1. URA3. LEU2. and HIS3. Other sequences with similar functions will be known to those of skill in the art.

Preferably. one of the YAC vectors contains a positive selectable marker and one contains a negative selectable marker. Either vector may be used to clone either of the targeting segments. For example. one YAC plasmid into which the 5' terminal region of the target sequence is cloned. may contain the positive marker. TRP1. Yeast strains which contain this plasmid are positively selected by tryptophan prototrophy. Other positive selection markers include HIS3 and LEU2. The second YAC plasmid. into which the 3' terminal region of the target sequence is cloned. may contain the negative marker. URA3. The URA3 gene encodes orotidine-5'-phosphate decarboxylase. an enzyme required for the biosynthesis of uracil. Selection of ura3 cells (cells which have lost the URA3 gene or in which URA3 and TRP1 are unlinked) is accomplished by plating cells on media containing 5-fluoroorotic acid (5-FOA). This compound is converted to a toxic product killing URA3 cells (Boeke. et al.. *Molec. Gen. Genet.*, 197:345. 1984). Cells in which URA3 and TRP1 are linked (contain both genes on the same DNA fragment). will be sensitive to 5-FOA. These 5-FOA$^s$ cells will be cells in which homologous recombination results in a single YAC vector containing the target sequence. Other negative selectable markers include LYS2. CAN1 and CYH2.

The conditions under which homologous recombination occurs include both in vitro and in vivo cultures. The method of the invention can be effected in vitro using a composition having the appropriate repertoire of enzymes, such as a yeast cell lysate which allows all components to assemble through homologous recombination to yield a YAC vector containing the target sequence. Preferably, the method of the invention is performed in vivo in a eukaryotic cell, and most preferably in a yeast cell. A preferred yeast cell is a strain of *Saccharomyces cerevisiae*. The strain of yeast which is used will depend on the selective markers chosen for the YAC plasmids. For example, when the TRP1, CYH2 and URA3 genes are on the vectors, the strain should be trp1Δ63, trp-289 or trpΔ901, cyh2$^r$, and ura3-52 or ura3Δ1, respectively. Those of skill in the art will be able to choose the appropriate yeast strain which is compatible for selection with the particular marker present on the plasmid.

For in vivo homologous recombination, the target sequence and two vectors containing the targeting segments are introduced into a yeast host and homologous recombination occurs. Transformation of a yeast host cell with recombinant DNA may be carried out by conventional techniques which are well known to those skilled in the art. Typical methods of transformation in yeast cells include lithium acetate, spheroplast transformation (after forming a protoplast of the host cell), and electroporation.

The invention also provides a composition comprising a YAC vector which contains a target sequence. The composition is produced by homologous recombination according to the method of the invention. Preferably, the target sequence is a eukaryotic virus DNA sequence, which is most preferably infectious when re-introduced into a permissible eukaryotic host cell. However, other large segments of DNA, such as human chromosomal DNA or genomes of other higher organisms are included.

When the composition of the invention includes a virus DNA sequence the virus DNA is preferably infectious. Infectivity of the virus is easily tested by transformation of the DNA from a YAC-containing strain (after growth and amplification in the appropriate environment to increase the number of copies of the YAC) to a susceptible host. A susceptible or permissive host is one which is sensitive to infection by the virus. DNA is prepared from the yeast strain by standard methods (see for example, Cryer, et al., *Meth. Cell Biol.*, 12:39–44, 1975; Hoffman, et al., *Gene* 57:267–272, 1987), digested with the appropriate restriction endonuclease to excise the viral genome from the vector, and introduced into a susceptible or permissive host cell which will allow the viral DNA to be expressed to produce viral proteins, such as a wild-type or modified virion. Plaque formation on the transfected culture is indicative of infectivity of the virus.

When the host transformed with the amplified YAC DNA is a eukaryote, such methods of transfection of DNA as calcium phosphate co-precipitation, conventional mechanical procedures such as microinjection, electroporation, insertion of a plasmid encased in liposomes, or virus vectors, may be used. Preferably, the calcium phosphate co-precipitation technique is used. Eukaryotic cells can also be cotransformed with DNA sequences encoding the target sequence (e.g., virus genome) of the invention, and a second foreign DNA molecule encoding a selectable phenotype, such as the herpes simplex thymidine kinase gene. (*Eukaryotic Viral Vectors*, Cold Spring Harbor Laboratory, Gluzman ed., 1982). Examples of typical eukaryotic hosts which are used include COS, BHK, 293, and CHO cells.

In another embodiment, the invention provides a method for the production of a target DNA sequence which comprises culturing the composition of the invention (a YAC vector which contains a target sequence) under conditions which allow replication of the composition. Depending on the markers of the YAC plasmid, growth of YAC-containing yeast strains in a specific selective medium permits amplification of the YAC. For example, when the vector contains a conditional yeast centromere, CEN, and a HSV thymidine kinase gene, amplification can be effected on medium which contains thymidine, sulfanilamide and methotrexate and a carbon source (e.g., galactose). Those of skill in the art will know the appropriate selective medium to grow the YAC-containing yeast strain (see for example, Ausubel, et al., *Current Protocols in Molecular Biology*, Unit 13, Wiley Interscience, 1992). The invention also includes the yeast cell which contains the composition of the YAC vector and the target sequence. Preferably, the yeast cell is a strain of *Saccharomyces cerevisiae*.

The discovery of a method for producing target sequence such as full length virus genomic DNA in large quantity, provides a good source for genetic manipulation of the DNA. One method which allows genetic manipulation is the two-step gene replacement technique which exploits targeted homologous recombination in transfected cells to replace a selected segment of yeast DNA with mutant or exogenous sequences. An alternative procedure which is now available is direct gene replacement.

Figure 2B:
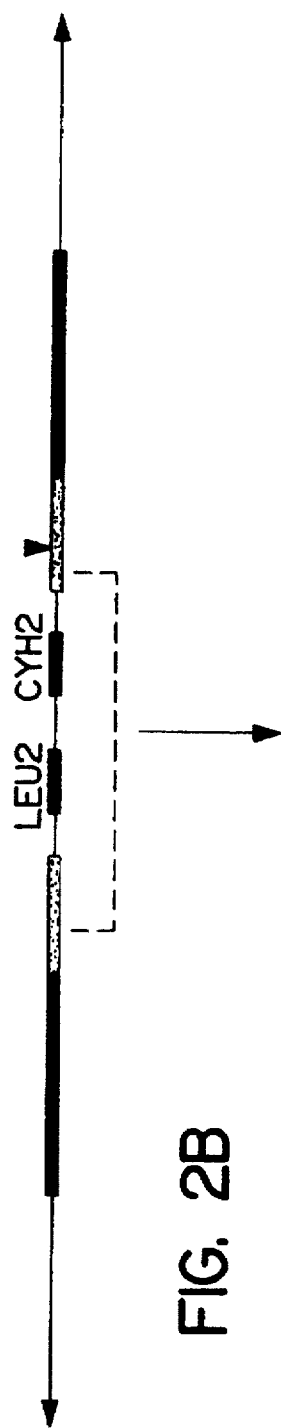
Figure 2C:
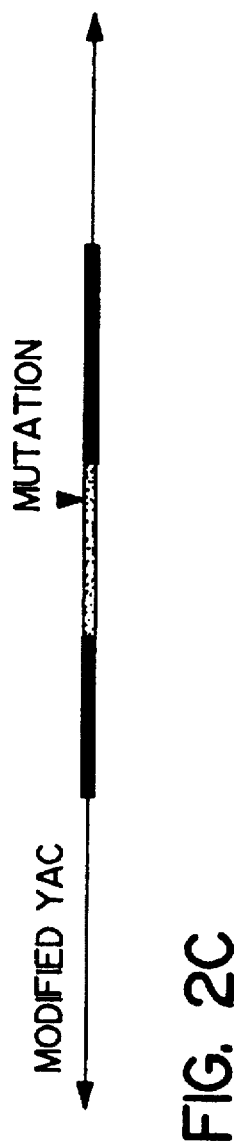
Figure 3:
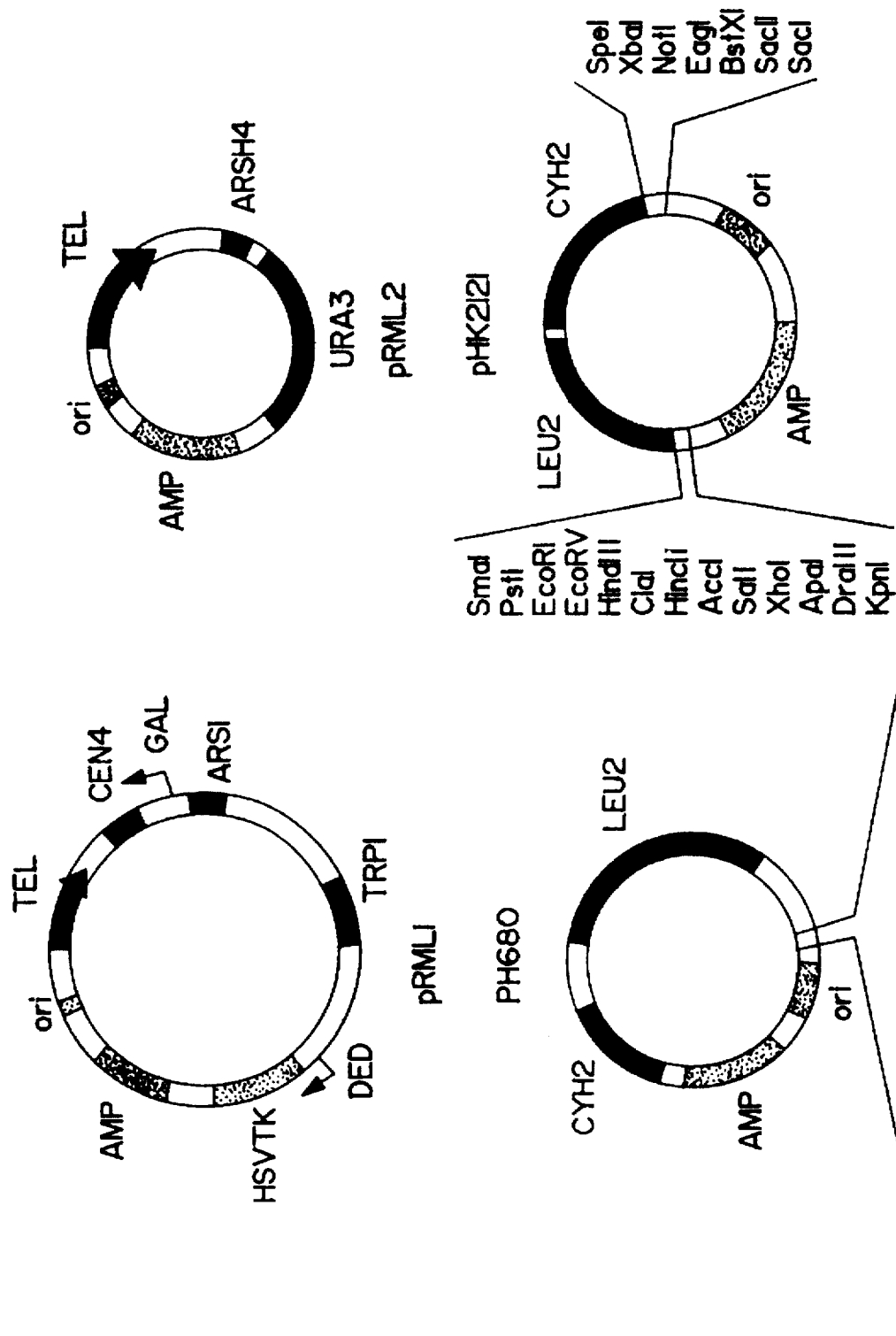
FIG. 3 is a diagram of the plasmids pRML1, PRML2, pPH680, and pHK2121.

For two-step gene replacement, a segment of DNA intended for incorporation into a YAC vector with a target sequence is first cloned into a plasmid which contains a positive and a negative selectable marker, as described above. (See schematic drawing, FIG. 2). For example, the segment of DNA desired for incorporation is cloned into the plasmid pPH680 (FIG. 3) which carries the yeast LEU2 and CYH2$^s$ genes. Other similar plasmids, such as pHK2121 (FIG. 3) are known to those of skill in the art. Segments of DNA must be homologous to sequences on the YAC target sequence (for example, mutant derivatives of YAC target sequences) or must be flanked in the plasmid (pPH680)-derived clone by homologous sequences. The pPH680 clone containing the DNA intended for incorporation is cleaved with a restriction enzyme within an area of homology and transformed into a yeast strain carrying the YAC vector with the target sequence. Within the transformed cells, recombination between the YAC target sequence and the plasmid containing the homologous sequence occurs at the site of restriction digestion and generates a new YAC containing an integrated copy of the pPH680 clone, including the LEU2 and CYH2$^s$ genes and the cloned segment (FIG. 2B); strains containing such YACs are selected for leucine prototropy. During subsequent growth of these strains, a second recombination event between the directly repeated sequences flanking the pPH680 vector results in the excision of the plasmid from the YAC. The excision event occurs at a frequency of about $10^{-2}$ to $10^{-3}$ per cell division. Strains in which excision occurs lose the CYH2s gene and can be selected for resistance to the drug cyclohexamide. In some cases, the DNA segment introduced on the pPH680 clone remains in the YAC in place of the homologous DNA originally present in the YAC. The result of these two recombinations is a stably-modified YAC carrying the modified insert sequences originally present in the pPH680 clone, and essentially no pPH680 vector sequences (FIG. 2C).

The above-described two-step gene replacement technique is useful in such cases where it is desirable to introduce a mutation into a virus which will serve as a vehicle for genetic therapy or vaccination, for example. The method is generally applicable to the construction of YACs containing any viral or other genomic DNA.

Figure 4A:
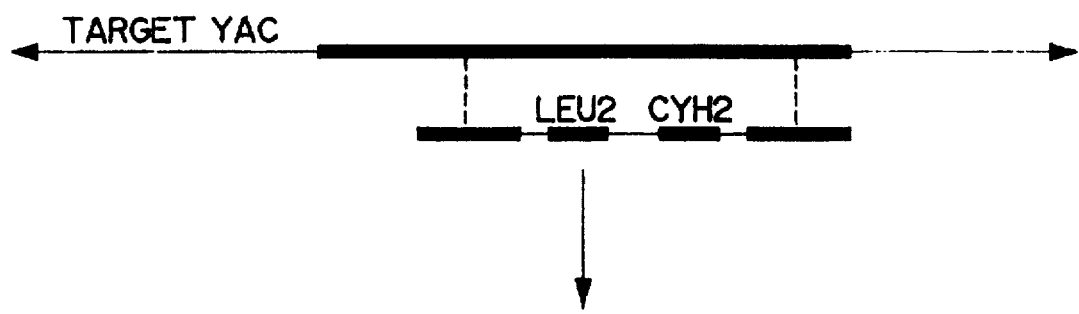
FIG. 4 (Parts A–C) is a schematic diagram of the direct gene replacement technique.
Figure 4B:
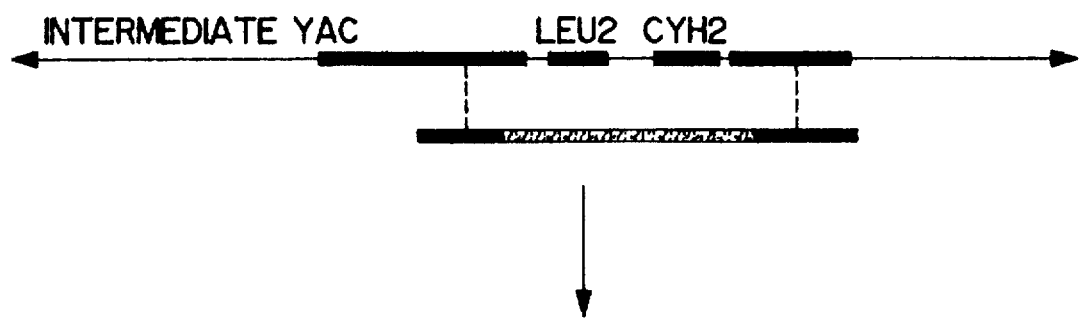
Figure 4C:

The discovery of a method for providing a source of target sequences, such as viral genomic DNA also allows genetic manipulation by a second technique, called direct gene replacement. This is an alternative procedure which exploits the same type of selections as described for the two-step gene replacement above and requires the construction of an intermediate YAC/target sequence vector carrying a selectable and non-selectable marker, for example LEU2 and CYH2$^s$. This is accomplished by transforming a target YAC-containing yeast strain with a DNA segment (prepared from a plasmid such as pPH680 or pHK2121, for example) containing LEU2 and CYH2$^s$ flanked by DNA sequences with homology to the YAC target sequence. Recombinationri between the target YAC and the fragment (FIG. 4A) replaces the target sequence on the YAC with LEU2 and CYH2$^s$ (intermediate YAC, FIG. 4B). Strains containing the intermediate YAC are selected for leucine prototrophy (or other substrate, depending on the marker). The LEU2 and CYH2$^s$ markers are then replaced with the segment to be introduced into the YAC target sequence, by recombination within the flanking sequences between the intermediate YAC and a DNA fragment introduced by transformation (FIG. 4B). Stable cyclo-hexamide-resistant (or other drug, depending on the marker) YACs with replacements identical to those that can be generated by the two-step technique are produced (FIG. 4C).

The following examples are intended to illustrate but not limit the invention. While they are typical of those that might be used, other procedures known to those skilled in the art may alternatively be used.

EXAMPLES

A yeast artificial chromosome (YAC) containing an infectious human adenovirus type 2 genome was produced by homologous recombination in vivo between adenovirus 2 virion DNA and YAC vector plasmids carrying segments of the viral left and right genomic termini. A mutant derivative of the YAC was produced by a gene a replacement technique that also exploits homologous recombination, and mutant virus were recovered from the modified YAC. The strategies used to create and to modify the adenovirus YAC are generally applicable to the construction and manipulation of YACs containing other DNA segments, such as the genomes of other viruses. In addition, the recombinational cloning approach proved to be efficient, and may permit the targeted cloning of segments of the genomes of higher organisms.

Example 1

Construction of Adenovirus YACs

The adenovirus YACs were constructed by recombination in vivo between Ad2 virion DNA and YAC vector plasmids containing the viral genomic termini. Spheroplasts of the yeast strain YPH857 (Mat a, ade2-101, cyh2$^r$, leu2Δ1, lys2-801, his3Δ200, trp1Δ63, ura3-52) were transformed with equimolar quantities of Ad2 DNA prepared from virus particles (Challberg, et al., *Virology*, 114:196, 1981) and linearized forms of the plasmids pRML1Ad2L and pRML2Ad2R. These plasmids consist, respectively, of the left and right Ad2 genomic termini cloned in the YAC vectors pRML1 and pRML2 (FIG. 3), which supply the cis-acting genetic elements required for YAC maintenance in yeast (telomeres, a centromere, and origins of replication), and genetic markers used to select yeast cells containing the YAC (TRP1 and URA3). pRML1, which was derived from pCGS966, contains a centromere subject to conditional inactivation and a gene (the herpes simplex virus thymidine kinase gene under control of the yeast DED1 promoter) that can be selected at increased copy number. These provide a system that permits amplification of the YAC by growth of YAC-containing yeast strains under selective conditions (Smith, et al., *Proc. Natl. Acad. Sci.*, 87:8242, 1990).

pPRML1Ad2L was made by inserting a 1 kb segment of Ad2 DNA containing the left genomic end between EcoR1 and ClaI sites of pRML1; pRML2Ad2R was made by inserting a 1.5 kb Ad2 DNA segment containing the right genomic end between the BclII and EcoRI sites of pRML2. Both viral fragments were produced by the polymerase chain reaction (PCR) from Ad2 virion DNA, and both contained a SnaBI site immediately adjacent to the viral terminal sequences. A single genomic terminal primer (5' CCGAATTCTACGTACATCATCAATAATATACC 3'; adenoviral sequences underlined) was used to amplify both fragments. The sequence of the viral protion of this primer differs from the published Ad2 sequence by the insertion of an A residue at position 8 (bold, above). In addition to viral sequences, the terminal primer contained EcoRI and SnaBI sites. The left hand internal primer covered Ad2 nucleotides 988–1005 and included a C/al site used for cloning. The right-hand terminal primer covered Ad2 nucleotides 34357–34374. The BglII site used in cloning this fragment is present at position 34390 in Ad2 DNA. (Roberts, R. J., et al., *Adenovirus DNA: The Viral Genome and Its Expression*, Martinus Nijhoff Publishing, Boston, 1986, p 1–51). The viral fragments are oriented in the two plasmids so that cleavage at a unique restriction site in each generates a linear molecule with the telomere at one end and the viral sequences, internal nucleotides exposed, at the other.

Each transformation contained 150 µl of spheroplasts, 6.7 µg of adenovirus 2 DNA, 2.0 µg of pRMLAd2L DNA, and 1.2 µg of pRML2Ad2R DNA. Plasmid DNAs were linearized by digestion with ClaI and BglII, respectively. Viral DNA was purified from CsCI-banded virions by digestion with pronase in the presence of SDS and phenol extraction (Challberg, et al., supra.). Selective medium contained 800 µg/ml thymidine, 1 mg/ml sulfanilamide, and 10 µg/ml methotrexate, with galactose as the carbon source. Cultures were inoculated with 10$^4$ cells/ml; growth to saturation took 3–5 days at 30°.

Figure 5:
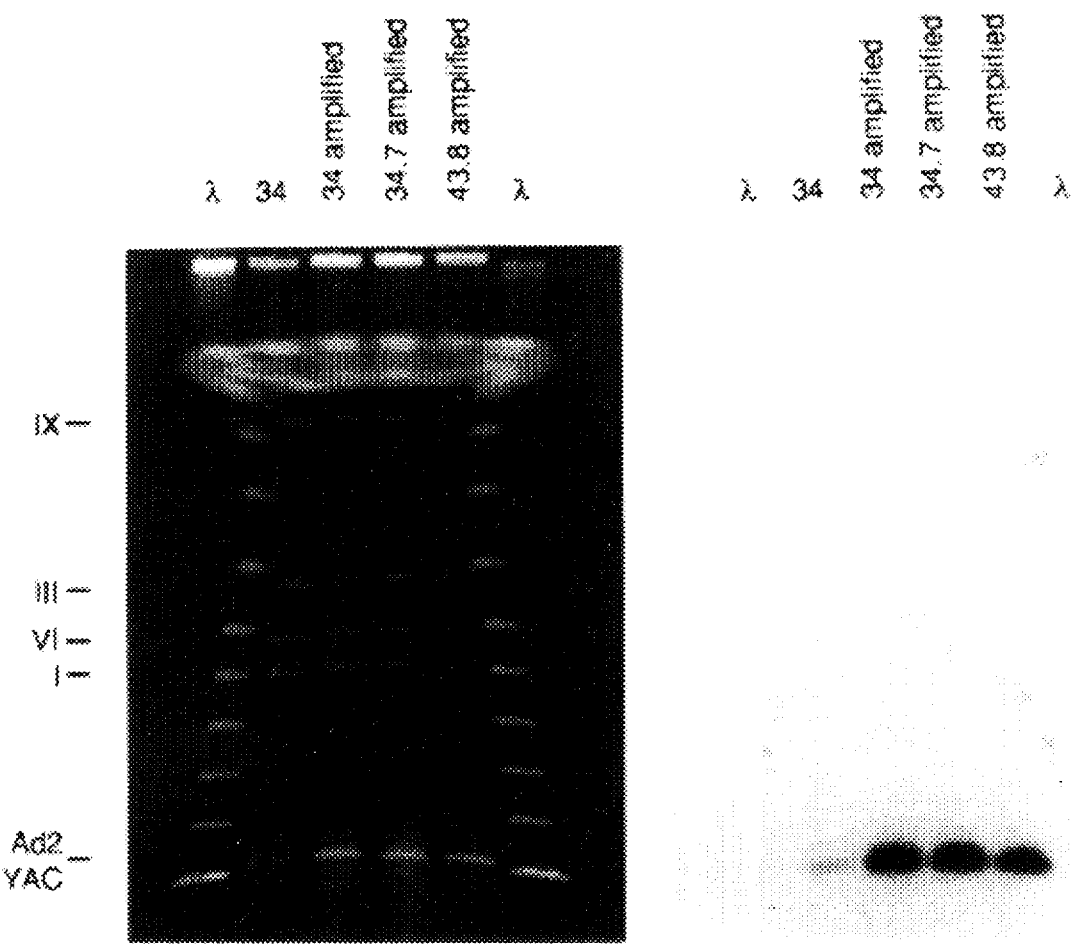
FIG. 5 shows an ethidium bromide stained OFAGE gel (left panel) and Southern blot analysis with labeled Ad2 virion DNA of FOA$^s$ transformants.
Figure 6:
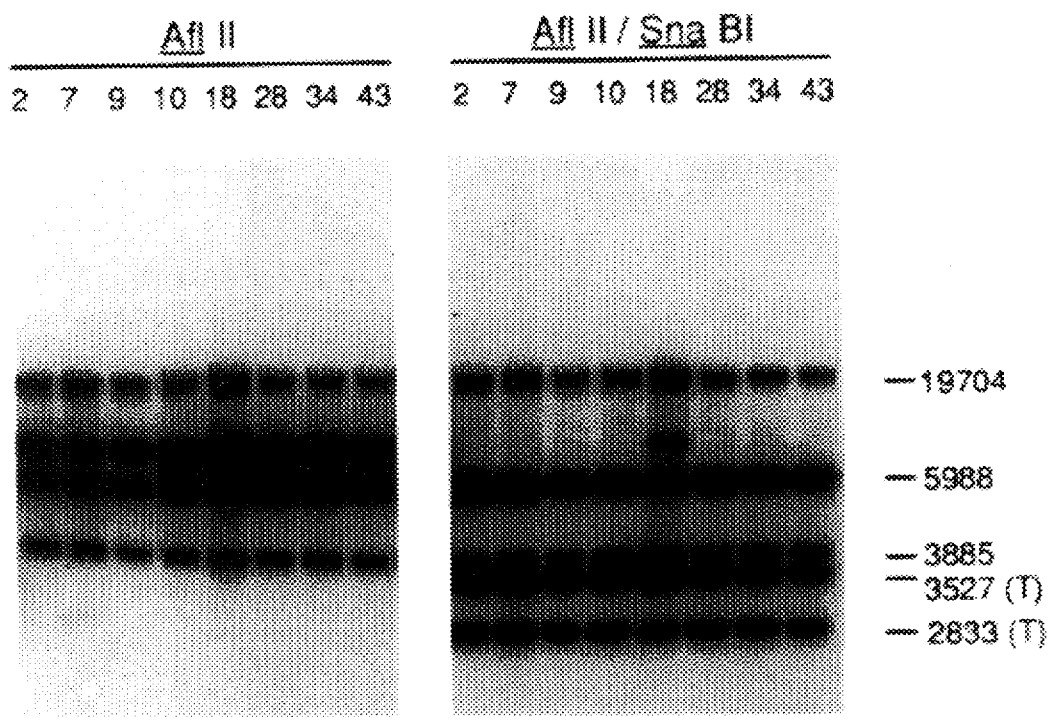
FIG. 6 is an autoradiogram showing the 55 kb YAC-Ad2 virion DNA after digestion with AflII and SnaBI or AflIII.
Figure 7A:
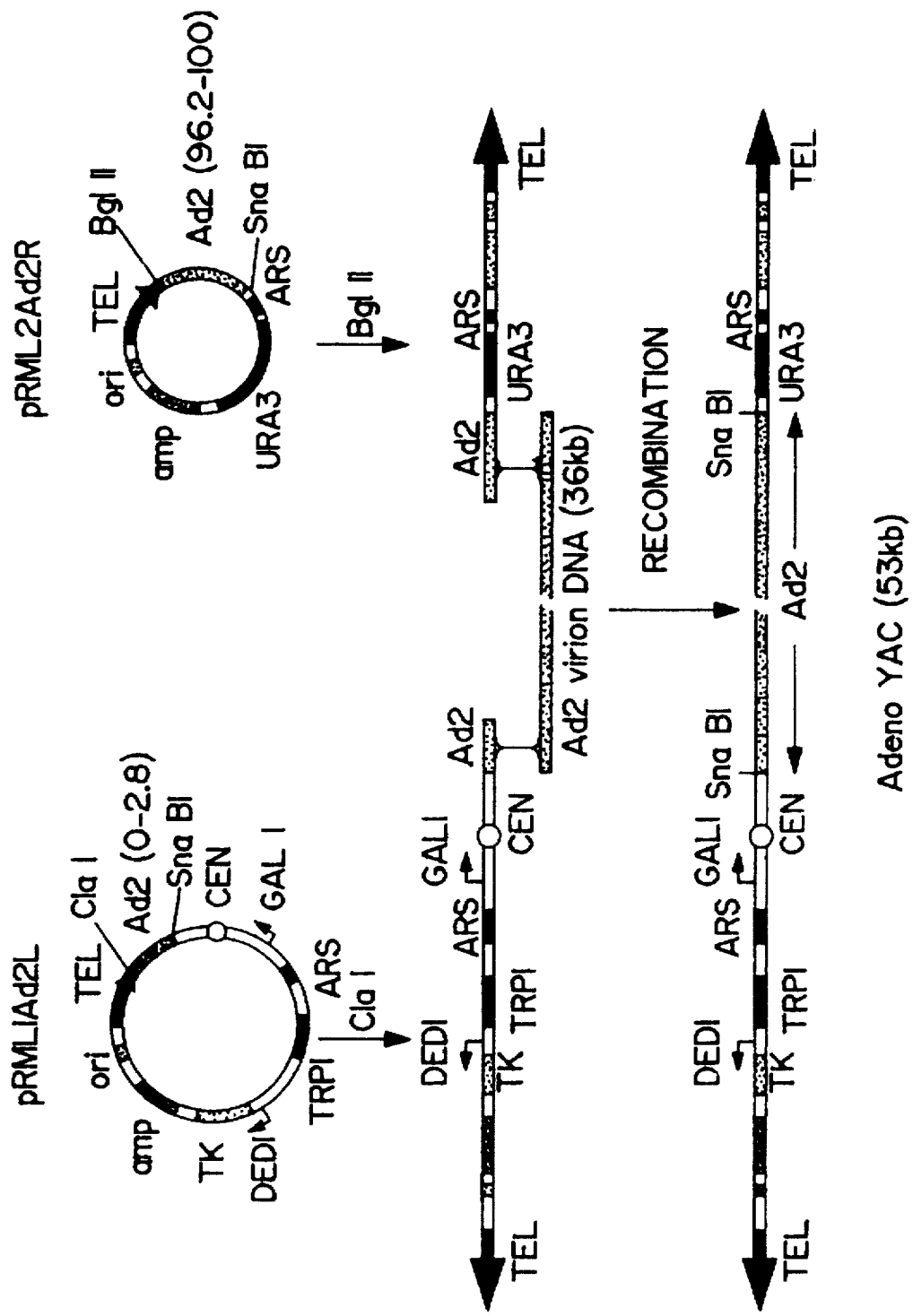
FIG. 7 (Parts A–B) 7A shows homologous recombination leading to a YAC-Ad2.
FIG. 7B shows the structure of the adenovirus YAC. ARS (autonomously replicating sequence): yeast origin or replication; CEN: yeast centromere; DED1: yeast DED 1 promoter; GAL4: yeast GAL4 promoter; HSV TK: herpes simplex virus thymidine kinase gene; S:Sna BI restriction endonuclease cleavage sites; TEL: yeast telomere; TRP1: yeast TRP1 gene; URA3: yeast URA3 gene.
Figure 7B:
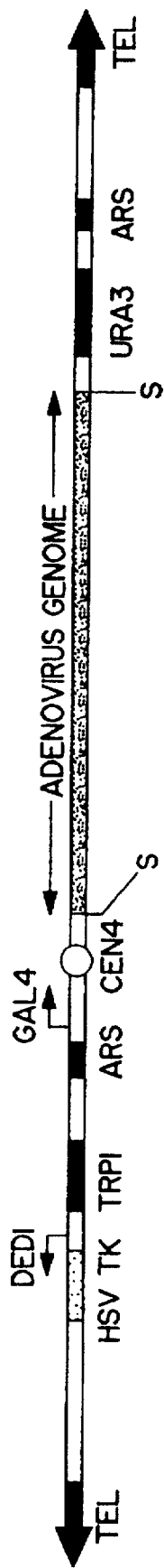

After transformation, TRP1 URA3 transformants were selected, colony purified, and examined to identify YAC-containing strains. In strains that contain an adenovirus YAC with the expected structure, the TRP1 and URA3 markers will be linked. To test linkage, transformants were plated under selection for TRP1 only, and the resulting colonies were replicated on medium that selects for TRP1 and against URA3 (using 5-fluoroorotic acid; FOA). These conditions reveal transformants in which URA3 and TRP1 are unlinked; such strains can lose URA3 while retaining TRP1, and will produce TRP1 ura3 (FOA$^r$) segregants. Of the transformants tested, 47 of 48 yielded no FOA-resistant segregants, suggesting that URA3 and TRP1 are linked in these strains. Ten transformants were then examined by pulsed-field gel electrophoresis (OFAGE) (Schwartz, et al. *Cell*, 37:67, 1984) and Southern transfer hybridization to determine whether they contained a YAC of the expected size carrying adenovirus DNA sequences. Nine of the transformants produced a band at 55 kb, the size of the predicted adenovirus YAC, both in ethidium bromide-stained gels and in autoradiograms made after transfer and hybridization to labeled Ad2 virion DNA (FIG. 5). Two of these showed either one or three additional bands (90–150 kb). The tenth strain showed a single faint band of about 150 kb. Finally, DNA was prepared from the eight transformants that contained a 55 kb OFAGE band, and was examined by Southern transfer hybridization after digestion either with AflII and SnaBI or AflII alone (FIG. 6). All eight transformants produced the five fragments characteristic of Ad2virion DNA when digested with both enzymes: SnaBI excises an intact viral genome from the YAC, which then yields a standard viral AflII restriction pattern. When digested with AflII alone, all eight transformants produced the three internal viral DNA fragments and a novel band of about 9000 bp. The latter band corresponds to the expected sizes, both about 9 kb, of the fragments that span the joints between the viral genomic termini and adjacent YAC sequences. These data are consistent with the interpretation that nearly all of the original TRP1 URA3 transformants contain an adenovirus YAC with the structure diagrammed in FIG. 7A and 7B, created by homologous recombination between viral sequences carried on the linearized YAC vector plasmids and Ad2 virion DNA.

Figure 8:
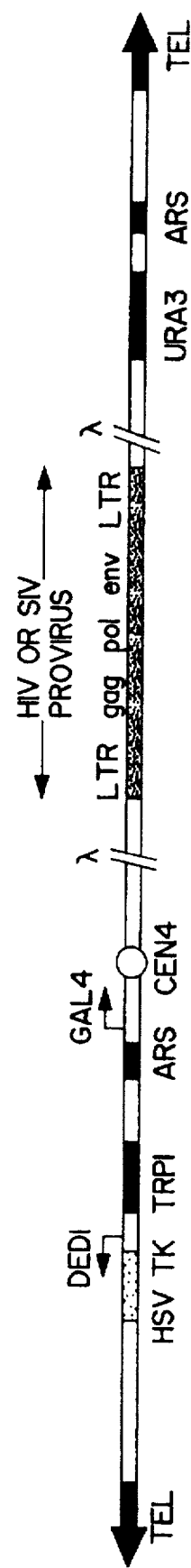
FIG. 8 shows the structure of the HIV and SIV YAC. ARS (autonomously replicating sequence): yeast origin or replication; CEN: yeast centromere; DED1: yeast DED1 promoter; env: envelope gene; GAL4: yeast GAL4 promoter; gag: gag gene; HSV TK: herpes simplex virus thymidine kinase gene; LTR: long terminal repeat; pol: polymerase gene; TEL: yeast telomere; TRP1: yeast TRP1 gene; URA3: Yeast URA3 gene; λ: bacteriophage lambda DNA.

YACs containing human immunodeficiency virus (HIV) or simian immunodeficiency virus (SIV) genomic proviral DNA were produced as described for adenovirus. Briefly, the HIV and SIV YACs were made from infectious clones in lambda phage obtained from the AIDS Research Reference Reagent Program. The DNA sequences which served as targeting segments were lambda genomic sequences from nucleotides 1650–2630, for the left terminal end, and 45175–45970, for the right terminal end. These were cloned into pRML1 and pRML2, respectively. The YAC-HIV or YAC-SIV was produced by homologous recombination as described above for production of YAC-Ad2. However, the resulting YAC-HIV or YAC-SIV contains the HIV or SIV flanked by lambda phage DNA sequences (FIG. 8).

Example 2

Infectivity of Cloned Viral Sequences

To test the infectivity of the cloned viral sequences, high molecular weight DNA was prepared (Rose, et al., *Methods in Yeast Genetics*, a Laboratory Course Manual, Cold Spring Harbor Laboratory Press, Cold Spring Harbor, N.Y. 1990, pp 133–135) from three YAC-containing strains after growth in selective medium (see Example 1) to increase the number of copies of the YAC present in the culture. As judged by comparison of the intensity of the amplified YAC band to that of the smallest yeast chromosome on an OFAGE gel, amplification of the YACs in these strains is consistently about five fold (FIG. 5). DNA extracted from each of the three strains was digested with SnaBI to excise the viral genome, and the digested DNA was introduced into 293 cells by $CaPO_2$ transfection. Plaques arose on transfected dishes at a frequency of 2 to 10 plaques per µg of total yeast DNA. Assuming 5 copies of the adenovirus YAC per cell after amplification, this corresponds to an efficiency of about 200–1000 pfu/µg of viral DNA, identical to that obtained for deproteinized virion DNA in parallel transfections. SnaBI digestion was essential for infectivity. The viral DNA produced by cleavage of a YAC with Sna BI will contain a three base remnant of the Sna BI site at each end; apparently, these extra bases do not significantly reduce the infectivity of the excised genome.

Example 3

Introduction of Mutations into YAC/Viral DNA

A variety of techniques have been developed for the genetic manipulation of YACs and natural chromosomes in yeast cells. One of these, two-step gene replacement, exploits targeted homologous recombination in transfected cells to replace a selected segment of yeast DNA with mutant or exogenous sequences (FIG. 2). To confirm the suitability of the adenovirus YAC for manipulation by such techniques, two-step gene replacement was used to introduce a deletion of Ad2 nucleotides 28404–30801 into the E3 region of the YAC. pHK2121 was constructed by insertion of two PCR fragments, covering Ad2 residues 27410–28404 and 30801–31825, into pPH680 between its XhoI and SalI, and XbaI and SacII sites, respectively. PCR primers included the restriction sites used for cloning and covered Ad2 sequences 27410–27426; 28404–28388; 30801–30819; and 31825–31808) was cloned in pPH680, a plasmid specifically constructed for use in two-step replacements in conjunction with markers present in YPH857. The resulting plasmid, pHK2121 (FIG. 3) was linearized by cleavage at its unique NdeI site (Ad2 residue 31076) and was introduced into a YAC containing strain by lithium acetate transformation, with selection for the pPH680 LEU2 marker. Linearization of pHK2121 within the Ad2 sequences targets recombination to that site, and LEU2 transformants should contain YACs with a complete copy of pHK2121 integrated at the Ad2E3 NdeI site. These YACs will carry two copies of E3, one wild-type and one mutant, separated by an integrated copy of the pPH680 plasmid.

Figure 9:
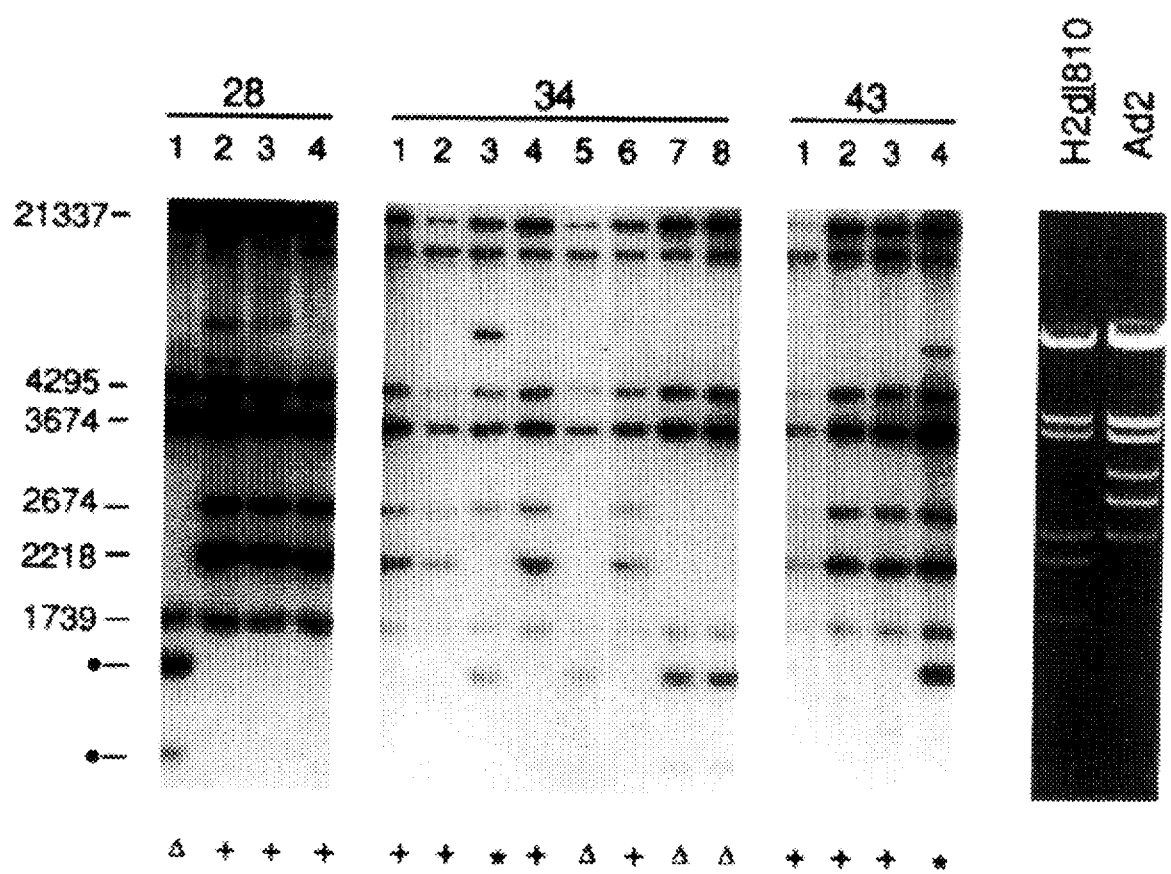
FIG. 9 shows a Southern blot analysis of YAC-Ad2-E3 mutants. Δ denotes deletion mutation; + denotes wild type YAC.

In addition to LEU2, pPH680 includes a dominant allele of CYH2 that confers sensitivity to cycloheximide ($CYH2^s$). Integrants therefore will be sensitive to the drug. During growth under conditions that do not select for retention of LEU2, occasional homologous recombinations between the tandemly duplicated E3 segments will excise the pPH680 sequences and one copy of E3 from the YAC. Such events will render the strain leu2 cyh$^r$, and depending upon the site at which recombination occurs, will generate a YAC bearing either a wild-type E3 or a deletion mutant derivative. E3 deletion mutant YACs therefore should be found among the cycloheximide resistant segregants. Several independent LEU2 CYH$^s$ transformants were grown to saturation in YPD (yeast extract, peptone, dextrose) broth to permit excision of the plasmid by recombination, and 100 µl portions of the YPD cultures were plated on medium that selected for URA3, TRP1, and cyh2$^r$. Sixteen segregants derived from two independently-obtained integrants were examined by Southern transfer hybridization. Ten of these contained a wild-type YAC (denoted by a (+) in FIG. 9) and 4 carried the E3 deletion mutation (denoted by a (Δ) in FIG. 9).

Virus was recovered by transfection of 293 cells with amplified, digested DNA prepared from two strains carrying deletion mutant YACs. The DNAs of 21 independently-obtained viral isolates were examined by restriction enzyme digestion and gel electrophoresis. All 21 isolates showed the restriction pattern expected for an E3 mutant. These experiments confirm that the adenovirus YAC can be manipulated by conventional yeast genetic techniques, and that viral mutants can be recovered from the manipulated YACs. The manipulation of the adenoviral viral genome in yeast has several advantages over conventional methods for the construction of mutants: it is applicable to any region of the viral genome, it is essentially independent of the placement of restriction sites in the viral DNA, and it eliminates the need for plaque purification of mutant virus. The speed of the process should make it particularly useful in preparing constructs that require successive modifications, such as the construction of multiple mutant or the refinement of viral vectors for gene delivery. If extended to other viruses, yeast genetic technology might in addition permit work with genomes unstable in E.coli, or too large to be conveniently manipulated in vitro or as an E.coli clone.

Example 4

Efficiency of YAC Formation

Recombinationally-targeted cloning from complex genomes requires the assembly of YACs by recombination between YAC vector plasmids and a target segment present in small amounts in a large excess of irrelevant DNA. To determine the efficiency of YAC formation under those conditions, a series of transformation experiments were performed in which decreasing amounts of Ad2 DNA mixed with mouse DNA were introduced along with constant amounts of linearized pRML1Ad2L and pRMLAd2R plasmid DNAs into YPH857 spheroplasts. The sum of the Ad2 and mouse DNA was kept constant, while the proportion of viral DNA in the mixture was varied from exclusively Ad2 to $1/10^5$ by mass. The latter is about equivalent to one copy of the viral genome ($3.6 \times 10^4$ bp) per mouse haploid genome equivalent ($3 \times 10^9$ bp). TRP1 LEU2 transformants arising from transformations with varying amounts of viral DNA were tested for linkage of URA3 and TRP1, for hybridization to an internal Ad2 DNA probe, and by OFAGE and conventional Southern transfer hybridization for the presence of an adenovirus YAC (Table 1).

YPH857 spheroplasts were transformed with linearized pPRML1Ad2L (2.8 μg) and pRML2Ad2R (1.2 μkg) DNAs, and with a total of 6.7 μg of a mixture of Ad2 and mouse DNAs. In different transformations, viral DNA comprised fractions of this mixture varying from 1 to $10^5$. The fraction of transformants in which URA3 and TRP1 were linked, the fraction that hybridized to an internal Ad2 DNA fragment, and the proportion of hybridization-positive strains that harbored an authentic adenovirus YAC Budged by size or structure) were determined for each transformation. For the organisms listed in the final column, a single-copy 36 kb DNA segment constitutes a fraction of the haploid genome equal to or larger than the fraction of the input DNA made up of Ad2 in the corresponding transformation. The frequency of transformation to TRP1 LEU2 was independent of the amount of adenovirus DNA present in the transformation. The number of transformants in which URA3 was stable under selection for TRP1 decreased with decreasing Ad2 DNA to a minimum of about 25% of transformants at a level of viral DNA corresponding to about 100 viral DNA molecules per mouse genome equivalent, and remained constant at lower levels and in the absence of Ad2 DNA. The fraction of transformants that hybridized to the Ad2 probe also decreased with decreasing input Ad2 DNA, to a frequency of 0.7% at 10 viral DNA molecules per mouse genome equivalent (line 5, Table 1). No hybridizing transformants were detected among 384 colonies screened in the transformation performed at 1 viral DNA molecule per mouse genome equivalent. Of the 3 strains from the 10 copy transformation identified by hybridization as candidates to harbor an adenovirus YAC, all contained a YAC of the expected size and/or with the expected structure as assessed by Southern transfer hybridization. Thus, it is possible to recover the adenoviral genome by recombinational YAC cloning at a level of representation of 10 copies per mouse genome equivalent of irrelevant DNA.

The recombinational cloning scheme employed to generate the adenovirus YAC has obvious application to other viral genomes, and has been used to produce infectious YAC clones of HIV and SIV. However, the method is in principle applicable to the cloning of any DNA segment as a YAC, if DNA fragments that bracket the target segment can be obtained. Further, the extremely high proportion of adenovirus-containing YACs found among the original transformants suggests that it may be possible to use the technique to clone specific segments of DNAs from sources in which the target is not the major component, such as the genomes of higher organisms.

These results indicate that appropriate applications of recombinational YAC cloning will not be limited to the cloning of purified DNA segments, but will include the isolation of specific segments from more complex DNAs. Because the efficiency of recombinational cloning may be affected by factors such as the size of the target and position of the physical ends of the target segment, the data obtained in this reconstruction experiment may only approximate the results that can be expected when cloning a segment from genomic DNA. Nevertheless, these results strongly suggest that for genomes of lower complexity than that of the mouse (such as D. melanogaster, C. elegans, and C. albicans), single copy genes can be obtained directly by recombinationallytargeted YAC cloning. In the reconstruction. YAC recovery declined in roughly linear fashion with decreasing Ad2 DNA content. Single copy segments in mammalian DNA therefore may be recoverable simply by increasing the screening effort (the expected yield is about 1 YAC per 1500 transformants). Alternatively, enrichment of target sequences (for example, by OFAGE), or refinement of the technique may permit recovery of YACs from mammalian DNA.

TABLE 1

EFFICIENCY OF YAC FORMATION

| Ad2DNA (fraction of input) | TRP1URA3 Linkage | Hybridization to an internal Ad2 probe | Authentic Viral YACs | Equivalent genome |
|---|---|---|---|---|
| 1 | 0.96 (52*) | | | |
| $10^{-1}$ | 0.75 (52) | 0.98 (52) | | |
| $10^{-2}$ | 0.56 (104) | | | E. coli |
| $10^{-3}$ | 0.24 (156) | 0.07 (156) | | C. albicans |
| $10^{-4}$ | 0.31 (156) | 0.007 (444) | 3/3 | D. melanogaster or C. elegans |
| $10^{-5}$ | 0.25 (312) | none (384) | | Mammals |
| none | 0.23 (52) | | | |

*Transformants screened

The invention now being fully described, it will be apparent to one of ordinary skill in the art that various changes and modifications can be made without departing from the spirit or scope of the invention.

What is claimed is:

1. A method of producing a yeast artificial chromosome (YAC) containing a foreign target DNA sequence comprising combining at least three DNA segments by homologous recombination under conditions which allow homologous recombination to occur, wherein the DNA segments comprise:

a) a target DNA sequence;

b) a first vector which contains a first targeting segment DNA sequence homologous to the 5' terminal region of the target DNA sequence; and c) a second vector which contains a second targeting segment DNA sequence homologous to the 3' terminal region of the target DNA sequence, wherein the combination of a), b) and c) produces a YAC.

2. The method of claim 1, wherein the homologous recombination is in vitro.

3. The method of claim 1, wherein the homologous recombination is in vivo.

4. The method of claim 1, wherein the homologous recombination is in a eukaryotic cell.

5. The method of claim 1, wherein the target sequence is a virus sequence.

6. The method of claim 1, wherein the first and second vector each contain a yeast telomeric sequence, a yeast origin of replication, and a selectable marker; and the first or second vector contains a yeast centromere.

7. The method of claim 4, wherein the eukaryotic cell is a yeast cell.

8. The method of claim 7, wherein the yeast is *Saccharomyces cerevisiae*.

9. The method of claim 5, wherein the virus sequence is proviral DNA from an RNA virus.

10. The method of claim 5, wherein the virus sequence is from a DNA virus.

11. The method of claim 5, wherein the virus sequence is infectious in a susceptible host.

12. The method of claim 9, wherein the RNA virus is a retrovirus.

13. The method of claim 12, wherein the retrovirus is human immuno-deficiency virus (HIV).

14. The method of claim 10, wherein the DNA virus is adenovirus.

15. A method of producing a yeast artificial chromosome (YAC) containing a foreign target DNA sequence comprising combining at least three DNA segments by homologous recombination under conditions which allow homologous recombination to occur, wherein the DNA segments comprise:

a) a target DNA sequence;

b) a first vector which contains a first targeting segment DNA sequence homologous to the 5' terminal region of the target DNA sequence, a yeast origin of replication, a yeast telomeric sequence, a selectable marker;

c) a second vector which contains a second targeting segment DNA sequence homologous to the 3' terminal region of the target DNA sequence, a yeast origin of replication, a yeast telomeric sequence, a selectable marker; and d) the first or second vector contains a yeast centromere, wherein the combination of a), b), c) and d) produces a YAC.

* * * * *